US00PP21092P2

(12) United States Plant Patent
Heuger

(10) Patent No.: US PP21,092 P2
(45) Date of Patent: Jun. 22, 2010

(54) ***HELLEBORUS* PLANT NAMED 'COSEH 220'**

(50) Latin Name: *Helleborus niger*
Varietal Denomination: COSEH 220

(76) Inventor: Josef Heuger, Postfach 11 03, D-49215 Glandorf (DE)

( * ) Notice: Subject to any disclaimer, the term of this patent is extended or adjusted under 35 U.S.C. 154(b) by 0 days.

(21) Appl. No.: 12/319,416

(22) Filed: Jan. 7, 2009

(51) Int. Cl.
*A01H 5/00* (2006.01)

(52) U.S. Cl. ..... Plt./439

(58) Field of Classification Search ..... Plt./439
See application file for complete search history.

*Primary Examiner*—June Hwu
(74) *Attorney, Agent, or Firm*—C. A. Whealy

(57) ABSTRACT

A new and distinct cultivar of *Helleborus* plant named 'COSEH 220', characterized by its upright and mounded plant habit; medium green-colored leaves; early and freely flowering habit; and large white-colored flowers.

1 Drawing Sheet

Botanical designation: *Helleborus niger.*
Cultivar denomination: 'COSEH 220'.

BACKGROUND OF THE INVENTION

The present invention relates to a new and distinct cultivar of *Helleborus* plant, botanically known as *Helleborus niger,* and hereinafter referred to by the name 'COSEH 220'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in December, 2002 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in November, 2004.

Asexual reproduction of the new *Helleborus* plant by divisions in a controlled greenhouse environment in Glandorf, Germany since February, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'COSEH 220'. These characteristics in combination distinguish 'COSEH 220' as a new and distinct cultivar of *Helleborus:*

1. Upright and mounded plant habit.
2. Medium green-colored leaves.
3. Early and freely flowering habit.
4. Large white-colored flowers.

Compared to plants of the parent selections, plants of the new *Helleborus* are more uniform and more freely flowering.

Plants of the new *Helleborus* can be compared to plants of *Helleborus niger* 'HGC Josef Lemper', disclosed in U.S. Plant Pat. No. 15,615. Plants of the new *Helleborus* differ primarily from plants of 'HGC Josef Lemper' in the following characteristics:

1. Plants of the new *Helleborus* have darker green-colored leaves than plants of 'HGC Josef Lemper'.
2. Plants of the new *Helleborus* have smaller leaves and flowers than plants of 'HGC Josef Lemper'.
3. Plants of the new *Helleborus* flower earlier than plants of 'HGC Josef Lemper'.

BRIEF DESCRIPTION OF THE PHOTOGRAPH

The accompanying colored photograph illustrates the overall appearance of the new *Helleborus* plant, showing the colors as true as it is reasonably possible to obtain in colored reproductions of this type. Colors in the photograph may differ slightly from the color values cited in the detailed botanical description which accurately describe the colors of the new *Helleborus* plant.

The photograph comprises a side perspective view of a typical flowering plant of 'COSEH 220' grown in a container.

DETAILED BOTANICAL DESCRIPTION

The aforementioned photograph and following observations, measurements and values describe plants grown in Glandorf, Germany in 15-cm containers during the winter in an outdoor nursery and under conditions which closely approximate commercial *Helleborus* production. During the production of the plants, day temperatures ranged from 5° C. to 32° C. and night temperatures ranged from 1° C. to 25° C. Plants had been growing for one year when the photograph and the description were taken. In the following description, color references are made to The Royal Horticultural Society Colour Chart, 2007 Edition, except where general terms of ordinary dictionary significance are used.

Botanical classification: *Helleborus niger* 'COSEH 220'.

Parentage:

*Female, or seed, parent.*—Unnamed proprietary seedling selection of *Helleborus niger*, not patented.

*Male, or pollen, parent.*—Unnamed proprietary seedling selection of *Helleborus niger*, not patented.

Propagation:

*Type.*—By divisions.

*Time to initiate roots.*—About 56 days at 4° C. to 15° C.

*Time to produce a rooted young plant.*—About six months at 12° C. to 15° C.

*Root description.*—Thick to thin, fleshy; white to brown in color.

*Rooting habit.*—Sparse.

Plant description:

*Plant form and growth habit.*—Herbaceous perennial; upright and mounded plant habit; moderately vigorous growth habit.

*Plant height.*—About 15 cm to 20 cm.

*Plant diameter* (*area of spread*).—About 30 cm to 35 cm.

Foliage description:

*Arrangement.*—Palmately compound with five to seven leaflets per leaf.

*Leaflet length.*—About 5 cm to 7 cm.

*Leaflet width.*—About 2 cm to 3 cm.

*Leaflet shape.*—Roughly ovate.

*Leaflet apex.*—Broadly acuminate.

*Leaflet base.*—Asymmetrically acute.

*Leaflet margin.*—Slightly serrate.

*Leaflet texture, upper and lower surfaces.*—Smooth, glabrous; leathery.

*Leaflet venation pattern.*—Pinnate; reticulate.

*Leaflet color.*—Developing leaves, upper surface: Close to 137C. Developing leaves, lower surface: Close to 146B. Fully developed leaves, upper surface: Close to 147A; venation, close to 146C. Fully developed leaves, lower surface: Darker than 147B; venation, close to 146C.

*Petiole.*—Length: About 5 mm to 15 mm. Diameter: About 2 mm to 3 mm. Texture, upper and lower surfaces: Smooth, glabrous. Color, upper surface: Close to 200B. Color, lower surface: Close to 146B to 146C; random spots, close to 200B.

Flower description:

*Flower shape and habit.*—Single rotate flowers; freely flowering habit, about 30 flowers developing per plant. Petals not observed.

*Fragrance.*—Moderately fragrant, pleasant.

*Natural flowering season.*—Early and long flowering period; plants flower from mid-November to February in Germany.

*Flower longevity on the plant.*—About three weeks; flowers persistent.

*Flower buds.*—Length: About 1 cm to 2 cm. Diameter: About 8 mm to 14 mm. Shape: Ovoid. Color: Between 155A to 145D.

*Flowers.*—Diameter: About 8 cm. Depth (height): About 2 cm.

*Sepals.*—Arrangement: About five to seven in a single whorl. Length: About 3.5 cm to 4 cm. Width: About 3 cm to 3.5 cm. Shape: Broadly ovate. Apex: Rounded to acute. Base: Obtuse. Margin: Entire. Texture, upper and lower surfaces: Smooth, glabrous; satiny. Color: When opening and fully opened, upper surface: Close to NN155D; color becoming closer to 144B to 144C with development; basal spot, close to 144A to 144B. When opening and fully opened, lower surface: Close to NN155D; basal spot, close to 144B.

*Peduncles.*—Strength: Strong. Length: About 20 cm. Diameter: About 4 mm to 6 mm. Aspect: Mostly upright. Texture: Smooth, glabrous. Color: Close to 145A to 145B; random spots, close to 187B.

*Reproductive organs.*—Stamens: Quantity per flower: About 200. Anther shape: Elliptical. Anther length: About 1 mm to 2 mm. Anther color: Close to 2A. Pollen amount: None observed. Pistils: Quantity per flower: About 15 to 18. Pistil length: About 1.5 cm. Stigma shape: Pointed. Stigma color: Close to 145C. Style length: About 8 mm. Style color: Close to 145D. Ovary color: Close to 145C to 145D. Nectaries: Quantity per flower: About 20 to 25. Length: About 8 mm to 10 mm. Shape: Salverform. Color: Towards the base, close to 144B; towards the apex, close to 4A. Seeds/fruits: Seed and fruit development have not been observed.

Garden performance: Plants of the new *Helleborus* have been observed to have good garden performance and to tolerate rain, wind and temperatures from about −10° C. to about 36° C.

Pathogen/pest resistance: Plants of the new *Helleborus* have not been shown to be resistant to pathogens and pests common to *Helleborus.*

It is claimed:

1. A new and distinct *Helleborus* plant named 'COSEH 220' as illustrated and described.

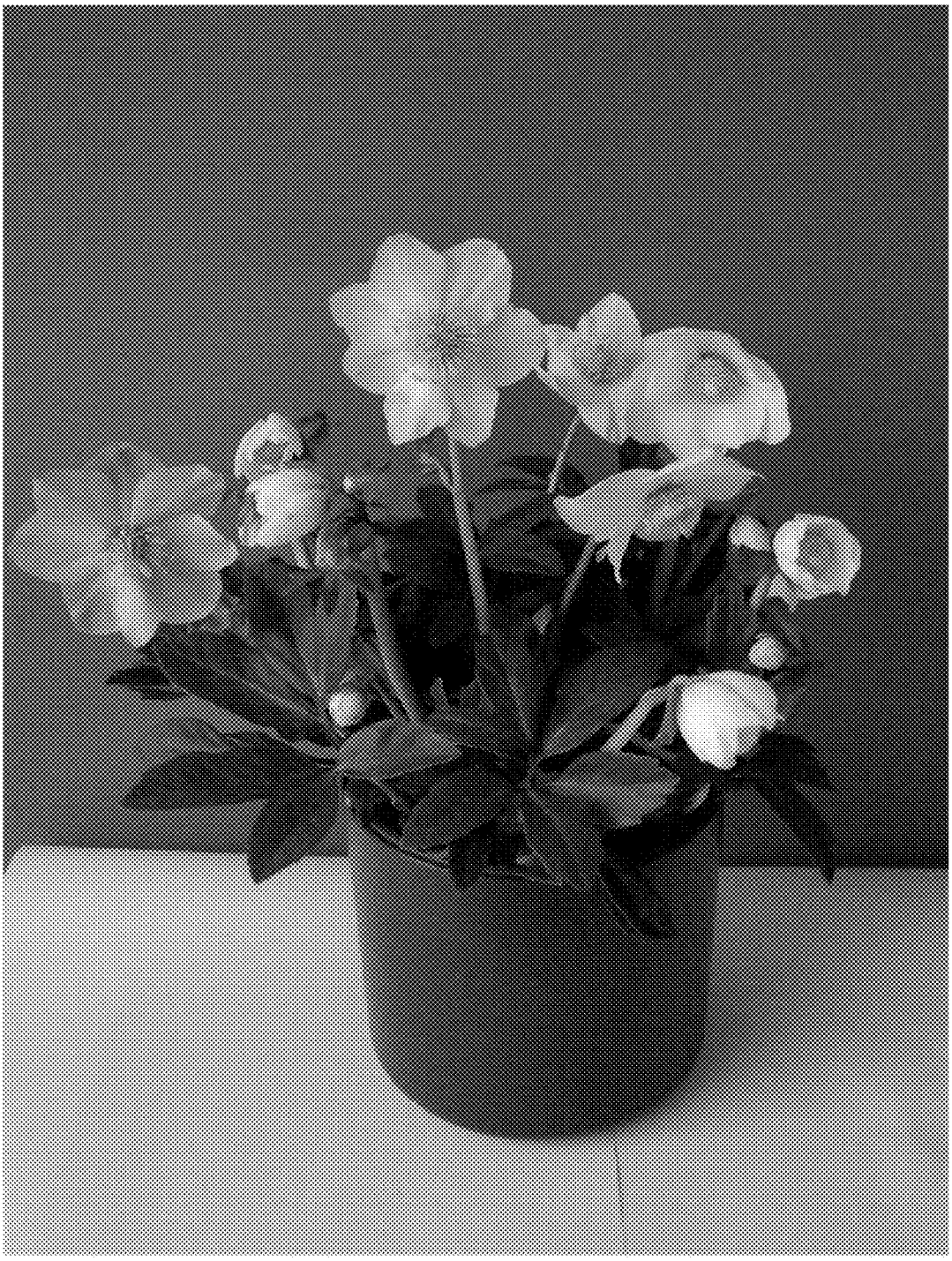

* * * * *